United States Patent
Cole et al.

(10) Patent No.: US 6,196,988 B1
(45) Date of Patent: Mar. 6, 2001

(54) METHOD OF FORMING A FLEXIBLE APPLICATOR FOR INSERTING AN ARTICLE INTO A MAMMALIAN BODY CAVITY

(75) Inventors: Robert T. Cole, Jackson, NJ (US); Andrew J. Hagerty, Doylestown, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/277,648

(22) Filed: Mar. 26, 1999

Related U.S. Application Data

(62) Division of application No. 08/885,719, filed on Jun. 30, 1997, now Pat. No. 6,019,743.

(51) Int. Cl.$^7$ ............................................. A61F 13/20
(52) U.S. Cl. ............... 604/11; 604/15; 493/269; 156/203; 156/217; 264/512; 264/513; 264/563
(58) Field of Search ............................... 604/11–18, 904, 604/285–288, 57–59, 311; 493/269; 156/203, 217, 212; 264/512, 513, 563

(56) References Cited

U.S. PATENT DOCUMENTS

| | | |
|---|---|---|
| 3,696,812 | 10/1972 | Jaycox . |
| 4,318,404 | 3/1982 | Cunningham . |
| 4,508,531 | 4/1985 | Whitehead . |
| 4,755,164 | 7/1988 | Hinzmann . |
| 4,822,332 | * 4/1989 | Kajander ................................ 604/16 |
| 5,158,535 | 10/1992 | Paul et al. . |
| 5,267,953 | 12/1993 | Paul et al. . |
| 5,395,308 | 3/1995 | Fox et al. . |
| 5,409,469 | 4/1995 | Schaerf . |
| 5,437,628 | 8/1995 | Fox et al. . |
| 5,709,652 | * 1/1998 | Hagerty ................................ 604/15 |

FOREIGN PATENT DOCUMENTS

| | | |
|---|---|---|
| 0 613 672 A1 | 9/1994 | (EP) . |
| 2 101 461A | 3/1972 | (FR) . |
| WO 96/37173 | 11/1996 | (WO) . |

* cited by examiner

Primary Examiner—Dennis Ruhl

(57) ABSTRACT

The present invention relates to a flexible applicator for inserting an article into a mammalian body cavity. The applicator has an elongate, hollow, structural member suitable for containing the insertable article, and an elongate expulsion member which is slidable within the structural member. The structural member has opposed inside and outside surfaces, and its length dimension is substantially greater than its width and height dimension. In addition, the structural member has a plurality of flex-enhancing elements which are arranged and configured to increase the lateral flexibility of the structural member.

11 Claims, 6 Drawing Sheets

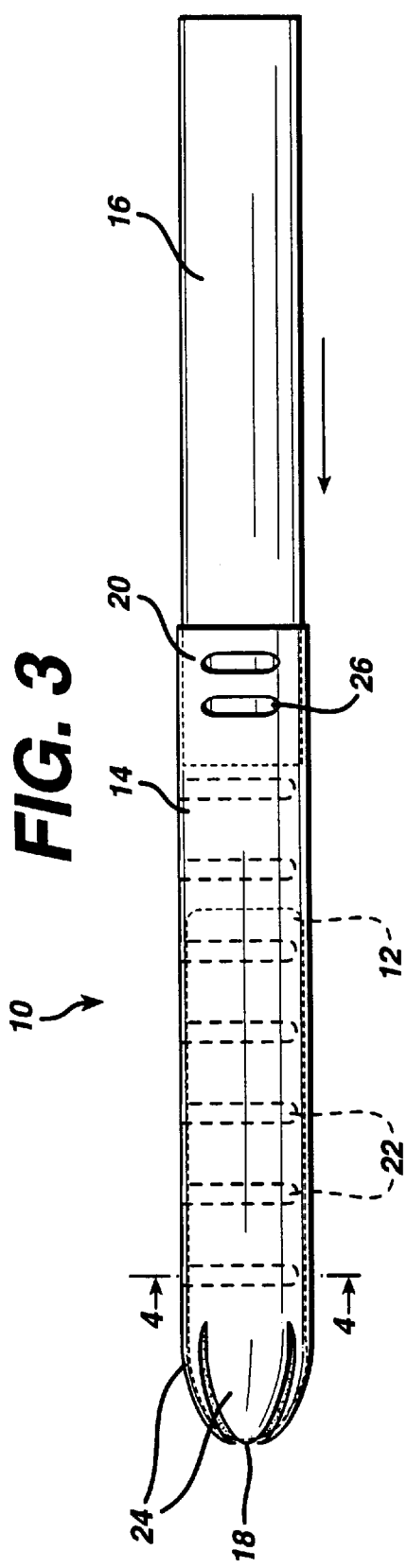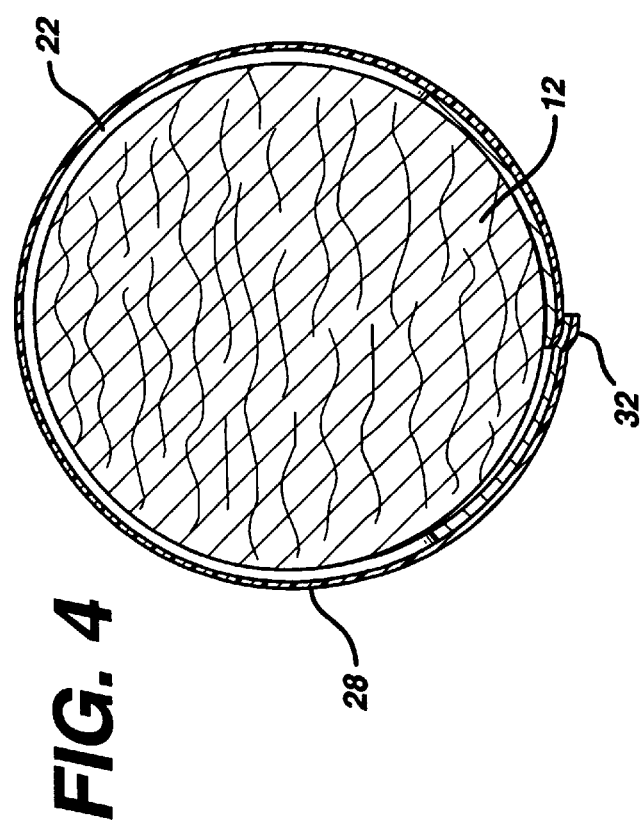

METHOD OF FORMING A FLEXIBLE APPLICATOR FOR INSERTING AN ARTICLE INTO A MAMMALIAN BODY CAVITY

This is a Divisional of prior application Ser. No.: 08/885,719, filed Jun. 30, 1997 now U.S. Pat. No. 6,019,743.

FIELD OF THE INVENTION

The present invention relates to flexible devices for inserting an article into a mammalian body cavity. In particular, the insertion device has an elongate, hollow structural member which has a plurality of flex-enhancing elements which increase its lateral flexibility.

BACKGROUND OF THE INVENTION

Hollow insertion devices, such as tampon applicators, are generally constructed of one of two basic materials: plastic and cardboard. While cardboard applicators are generally more rigid than plastic applicators, neither material easily conforms to the body cavity in which the applicator is inserted. Attempts to enable an applicator to more closely conform to a body cavity, such as a vagina, have included tampon applicators, such as those described in Paul et al., U.S. Pat. Nos. 5,158,535 and 5,267,953; and Fox et al., U.S. Pat. No. 5,437,628. Unfortunately, this approach suffers in two major areas: first, not all users have the same body shape, and second, the use of these curved devices requires the user to carefully orient the applicator during use. This must often be done in cramped bathrooms with poor visual control.

In view of the poor ability of the prior art to conform to many different body shapes, what is needed is an applicator device which is sufficiently rigid to permit insertion of an article into a body cavity and which also retains sufficient flexibility to conform to individual users' unique body shape.

SUMMARY OF THE INVENTION

The present invention relates to a flexible applicator for inserting an article into a mammalian body cavity. The applicator has an elongate, hollow, structural member suitable for containing the insertable article, and an elongate expulsion member which is slidable within the structural member. The structural member has opposed inside and outside surfaces, and its length dimension is substantially greater than its width and height dimension. In addition, the structural member has a plurality of flex-enhancing elements which are arranged and configured to increase the lateral flexibility of the structural member.

The flexible applicator of the present invention may be used as tampon applicators for feminine hygiene, or for the vaginal or rectal delivery of prophylactic compositions and/or medicaments.

The invention also relates to a method of forming a flexible applicator. In this method, flex-enhancing elements are formed in a structural member having an outer surface, a layer of a flexible material is superposed on the outer surface of the structural member, and the structural member is formed into an elongate, hollow member suitable for containing the insertable article. The hollow member has opposed insertion and gripper ends.

The flexible material may be laminated to the outer surface of the structural member by (i) applying a laminating material to the outer surface of the structural member and (ii) applying the flexible material to the laminating material.

BRIEF DESCRIPTION OF THE DRAWING

FIG. 3 is a side elevation of a tampon applicator according to the present invention.

FIG. 4 is a cross-section taken along line 4—4 of FIG. 3.

DETAILED DESCRIPTION OF THE PREFERRED EMBODIMENT

Figure 1:
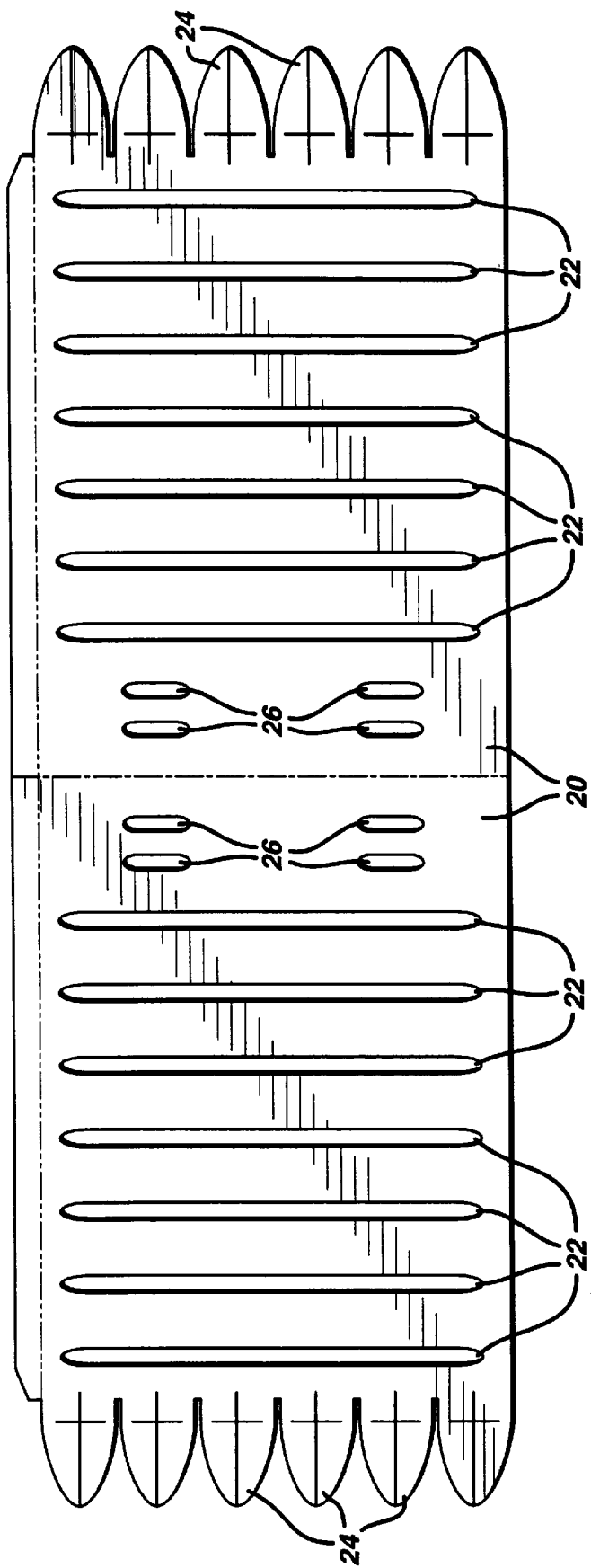
FIG. 1 is a plan view of a double blank useful in forming a tampon applicator according to the present invention which employs relatively narrow slots as the flex-enhancing elements.
Figure 2:
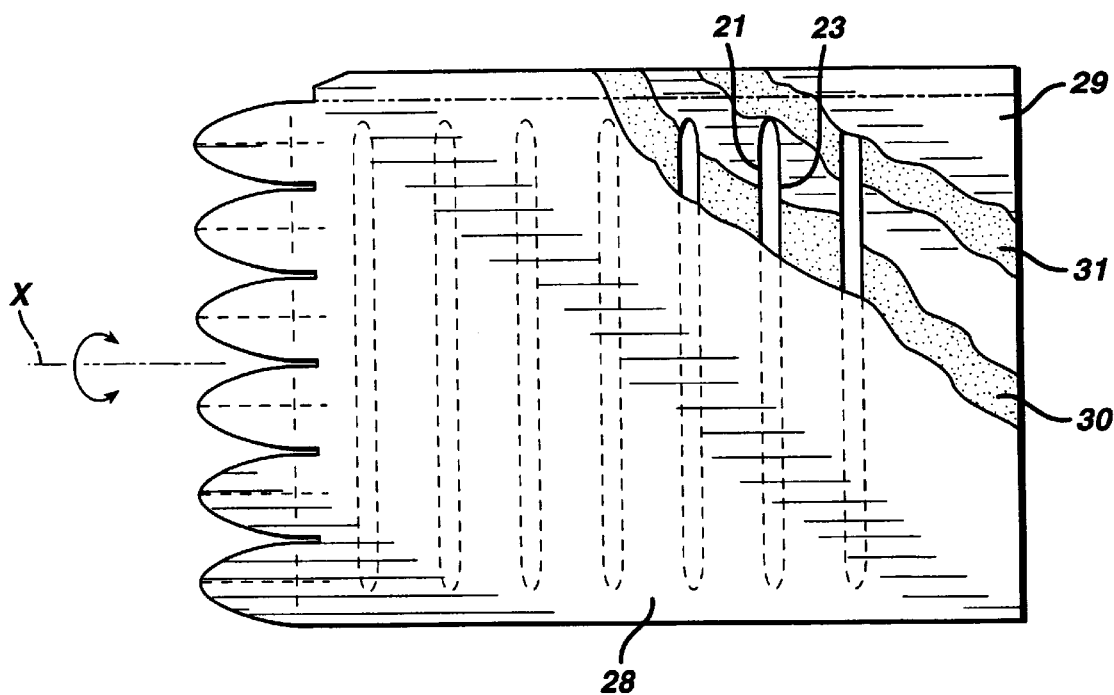
FIG. 2 is a partially cut-away plan view of a blank useful in forming a tampon applicator according to the present invention.

A preferred embodiment of the present invention is illustrated in FIG. 3, i.e., a tampon applicator 10 for vaginal insertion of a catamenial tampon 12. The tampon applicator 10 comprises an outer barrel 14 and a plunger 16 which is slidable within the barrel 14 to eject the tampon 12 therefrom. The barrel 14 is an elongate, hollow, structural member. It has opposed inside and outside surfaces, a length dimension which is substantially greater than its width and height dimensions, and opposed insertion 18 and gripper 20 ends. The barrel 14 also has a plurality of flex-enhancing elements (illustrated as slots 22) formed therein which are arranged and configured to increase its lateral flexibility. The plunger 16 may also incorporate flex-enhancing elements (not shown) into its structure to increase its lateral flexibility in a manner similar to the barrel 14.

The barrel 14 may also have a plurality of petals 24 formed at the insertion end 18 to allow the end to be substantially closed. The closure of the insertion end 18 can take on any configuration, including without limitation, domed, conical, elliptical, etc.

The gripper end 20 may have features to help the user grip the barrel more securely during use. These features are shown as large apertures 26, but they may also include raised structures, indentations or grooves, friction-increasing coatings, etc.

In a preferred embodiment, the barrel 14 also has a flexible material 28 disposed on its outside surface. This flexible material 28 may be attached to the barrel by an intermediate layer, such as an adhesive 30, to form a laminate, or it may be coated directly onto the outside surface of the barrel 14. Other methods of attaching the flexible material 28 to the barrel 14 will be readily recognized by one of ordinary skill in the art. In certain embodiments of the invention such as those of FIGS. 1–7 and 9, it may be appropriate to apply the laminating adhesive 30 onto the outside surface of the barrel 14 or barrel-forming material prior to applying the flexible material 28 thereto. In other embodiments, more conventional methods of coating and/or laminating may be used.

Optionally, a second flexible material 29 may be disposed on the inside surface of the barrel 14 by means of a second intermediate layer such as adhesive 31. This second flexible material 29 may help to reduce or eliminate the opportunities of the tampon 12 to be caught on the edges 21, 23 of perforated flex-enhancing elements.

Figure 8:
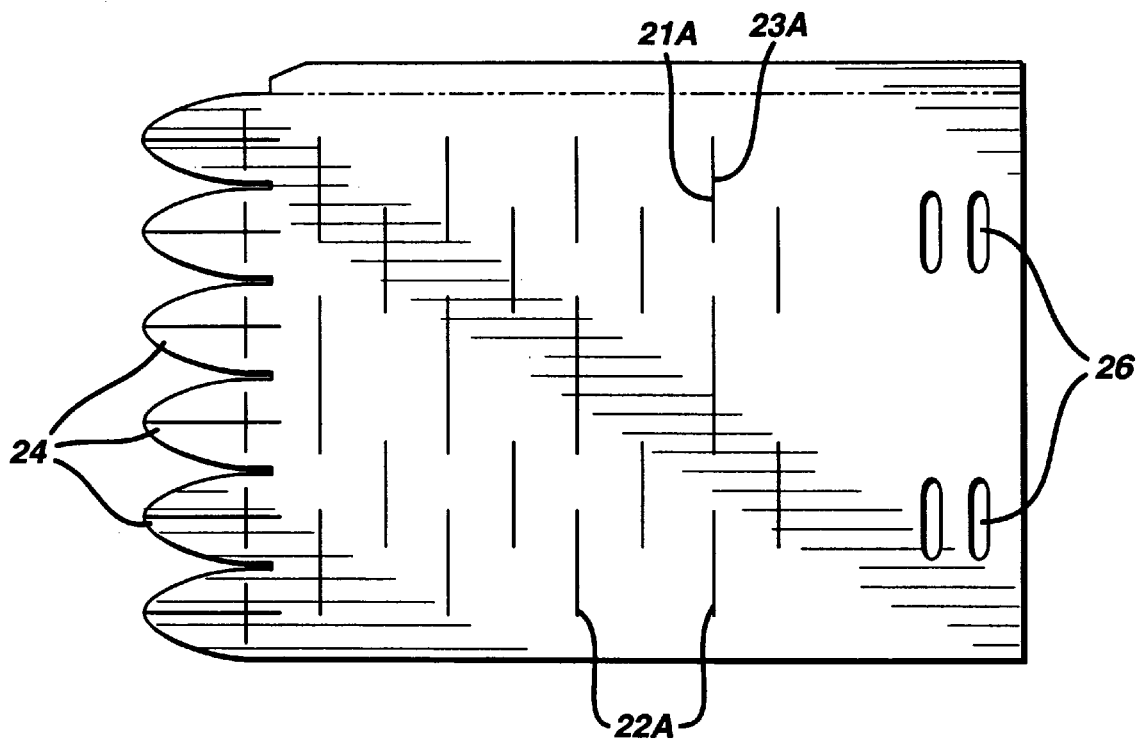
Figure 9:
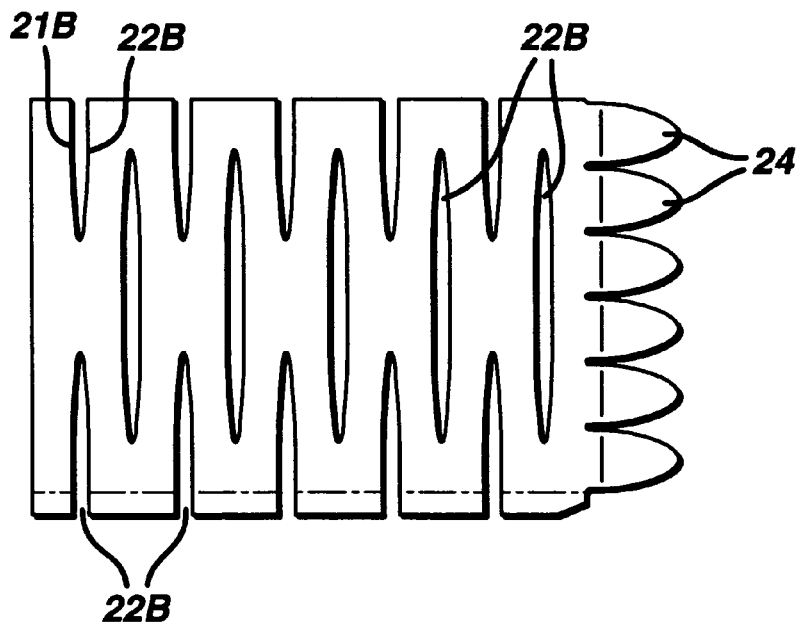

Flex-enhancing elements useful in the operation of the present invention include, without limitation, perforations, such as slits, slots, cut-outs, and the like (including perforations which extend through less than the complete thickness of the structural member or one or more layers in a laminate forming this member); folds, scores, and the like. Preferably, the flex-enhancing elements are disposed along the length of the barrel 14. They may either be aligned along this length, or they may be arranged in a substantially offset, alternating pattern. When the flex-enhancing elements are aligned along the length, the applicator 10 will generally have flexibility primarily in one plane through its central axis. When they are offset (as shown in FIGS. 8 and 9), the applicator will generally have flexibility in more than one plane.

When the structural member forming the barrel 14 has the preferred flexible material 28 disposed on its outside surface, the flex-enhancing elements may result in the segmentation of the structural member into discrete units such as short lengths of tube which are substantially shorter than their diameter. These segments will then be held together and maintained as a flexible barrel 14 by the outer flexible material 28 and optionally by the inner flexible material 29. The flex-enhancing elements may also be the result of a continuous spiral slit which results in a plurality of slits when viewed in longitudinal cross-section. Again, this type of flex-enhancing elements would benefit from the use of at least the outer flexible material 28 to hold the structural material together as a barrel 14.

The flex-enhancing elements are preferably arranged and configured to substantially maintain the longitudinal compressive strength of the structural member. Thus, the user is able to maintain control of the insertion device, especially the barrel 14, during its insertion into the body cavity.

Figure 5:
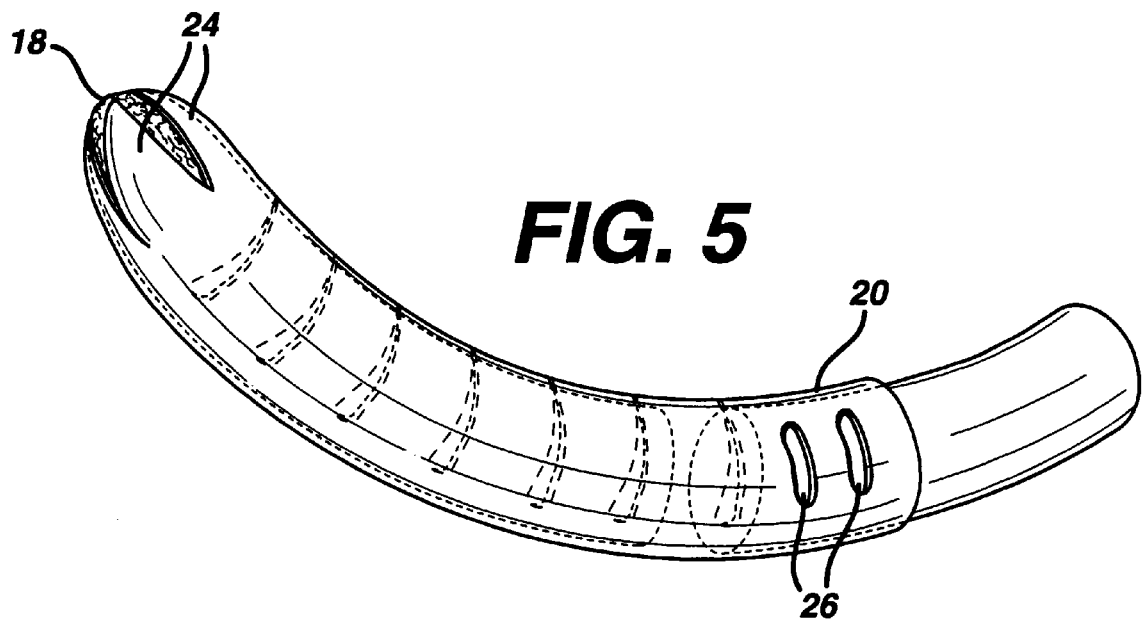
FIG. 5 is a perspective view of a tampon applicator according to the present invention which has been curved.
Figure 6:
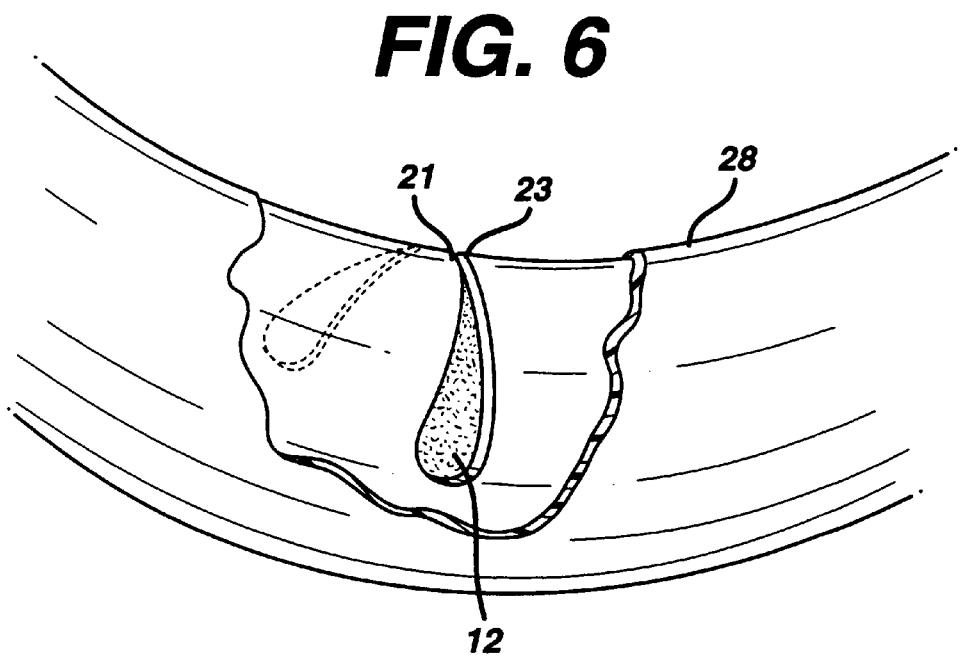
FIG. 6 is a partially cut-away, exploded view of a portion of the tampon applicator of FIG. 5.
Figure 7:
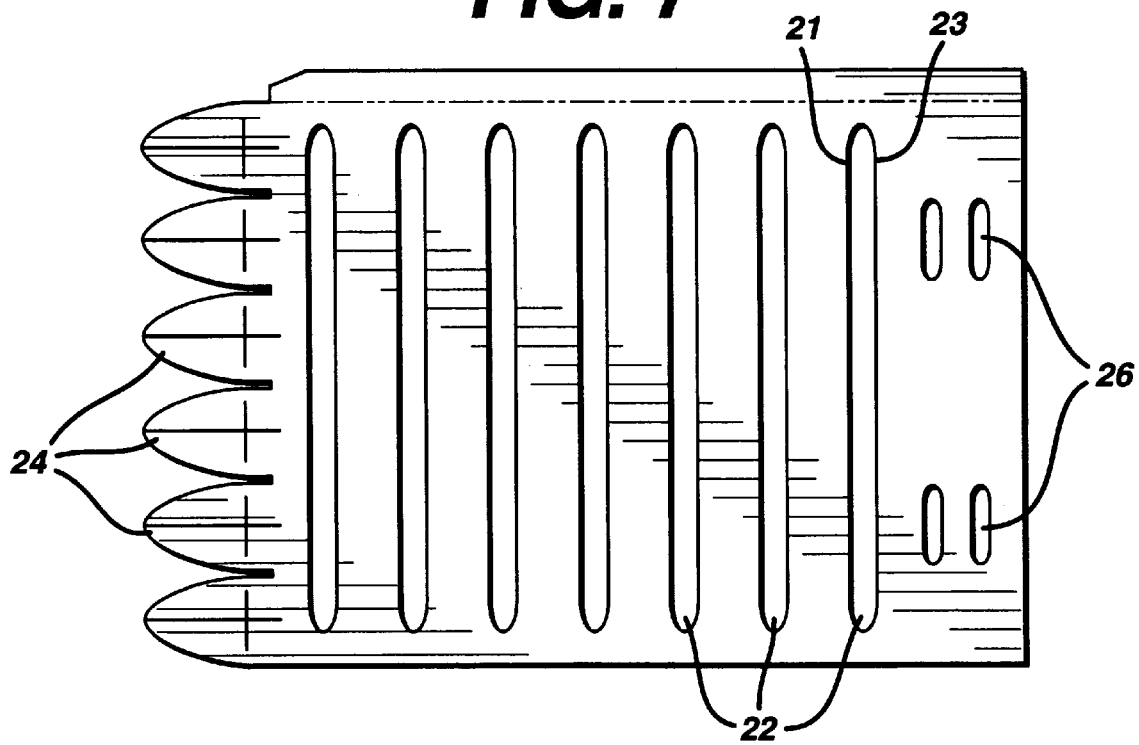
FIGS. 7–9 are plan views of alternative embodiment blanks useful in forming a tampon applicator according to the present invention which employ wide slots, slits, and cut-outs, respectively, as the flex-enhancing elements.

In a particularly preferred embodiment, the flex enhancing elements in the barrel 14 are perforations which have edges 21, 23. These perforations may have a major axis and a minor axis. Preferably, the major axis of the flex-enhancing elements is oriented substantially perpendicular to the length of the applicator. The edges 21, 23 of the perforations may abut (for example, the slits 22A shown in FIG. 8) or they may be separated (for example, the slots 22 shown in FIG. 3 and the cutouts 22B shown in FIG. 9) when the barrel 14 is in a relaxed, unstressed state. When the barrel 14 is subjected to forces having a component perpendicular to the longitudinal axis, the flex-enhancing elements allow the barrel 14 to flex into a curved orientation as shown in FIG. 5. In the curved orientation, the edges 21A, 23A of slits 22A will separate, while the edges 21, 23 of slots 22 will generally close as shown in FIG. 6. While this discussion focuses on flex-enhancing elements in the barrel 14, it is also applicable to flex-enhancing elements (not shown) in the plunger 16.

Figure 10:
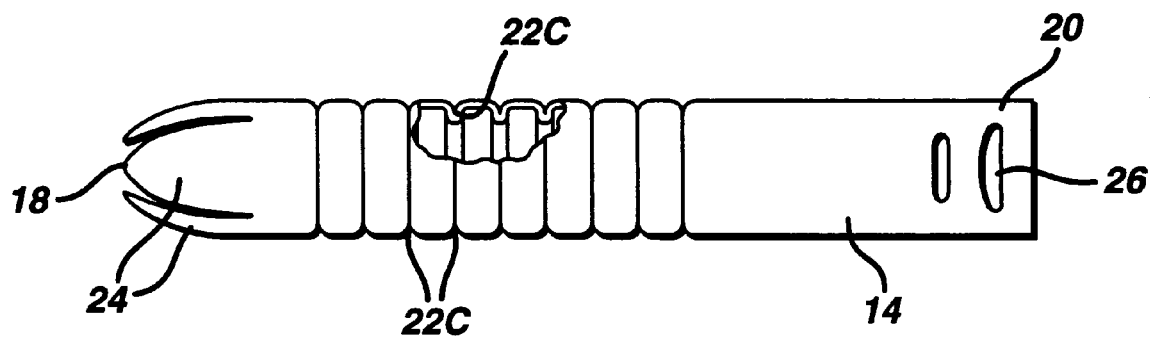
FIG. 10 is a partially cut-away side elevation view of an alternative embodiment of a tampon applicator according to the present invention which employs folds as the flex-enhancing elements.

In the alternative embodiment illustrated in FIG. 10, the flex-enhancing elements in the barrel 14 comprise a fold 22C. In this embodiment, the fold 22C is directed substantially inward from the outside surface of the barrel 14. This inward direction of the fold 22C allows the outside surface to remain substantially smooth. In this embodiment, it is likely that the tampon 12 will have a smaller diameter, or the barrel 14 will have a larger diameter to allow for the annular space occupied by the folds 22C.

The barrel 14 may be made of structural materials generally known to those of ordinary skill in the art. These materials include, without limitation, plastic sheet; moldable plastic, such as injection-moldable or blow-moldable plastic; biodegradable plastic, such as those disclosed in the commonly assigned application, Dabi et al., U.S. Ser. No. 08/006,013, filed Jan. 15, 1993 (herein incorporated by reference); and cardboard. The cardboard used as structural materials can be a single layer of cardboard material, or it can be a plurality of laminated layers to provide multiple benefits relating to the various layers. Useful cardboard stock for the formation of the tubular elements include, without limitation, paperboard, cardboard, cup stock, paper, and the like.

The structural material preferably has disposed thereon the flexible material 28 generally discussed above to provide aesthetics similar to conventional plastic-coated or plastic-laminated cardboard applicators. This flexible material 28 is preferably a substantially continuous layer which spans and is unsupported by the structural material at the flex-enhancing elements The flexible material 28 may be a plastic film, an elastomeric film, coated paper, and the like. Useful plastics include, without limitation, polyolefins such as polyethylene and polypropylene, polyesters such as polyethylene terephthalate, polycaprolactone, polyvinyl alcohol, ethylene-vinyl acetate copolymers, cellophane, and the like. Useful elastomers include, without limitation, natural rubber, styrene-butadiene copolymers, isobutylene-isoprene copolymers, polychloroprene systems (Neoprene Registered TM, duPont), polyurethanes, polysulfide rubbers, polyacrylate elastomers comprising the copolymerization of ethyl acrylate and acrylic acid-lower alkanol esters, nitrile rubber, butyl rubber, polysulfide rubber, polyisoprene, ethylene-propylene terpolymers such as EDPM rubber, silicone rubber, and the like. Useful coated papers include waxed paper, plastic-coated paper, silicone-coated paper, and the like.

Preferred structural materials include cardboards and laminated cardboards. These plastic laminated cardboard materials may include additional layers such as adhesive layers, tie layers, and the like.

Typical dimensions for the barrel 14 useful in tampon applicators include a length of about 5 to 8 cm, a diameter of about 8 to 16 mm, and thicknesses of about 0.4 to 0.6 mm. Preferably, the diameter of the plunger 16 is less than the diameter of the barrel 14 to allow for a telescopic arrangement of the plunger 16 within the barrel 14 as shown in FIG. 3.

The insertion device can be formed in several ways currently known to those of ordinary skill in the art. Tubular structural members may be formed as a continuous spiral-wound tube and subsequently cut to form the tubular elements. On the other hand, individual tubular elements or shorter tubes can be formed from rectangular sheets (or blanks) of cardboard. These blanks can be rolled about a central axis X in the manner indicated in FIG. 2 and secured with longitudinal seams 32 as shown in FIG. 4. This is shown in greater detail in Hinzmann, U.S. Pat. No. 4,755,164, herein incorporated by reference. Alternatively, they can be convolutely wound as disclosed in Whitehead, U.S. Pat. No. 4,508,531. The shorter tubes can be cut to form a small number of tubular elements, similar to the continuous, spiral-wound tubes.

In use, the user simply removes the tampon applicator 10 from any protective wrappers in which it may be packaged, holds the gripper end 20 and inserts the insertion end 18 of the applicator into the vagina. After insertion of the applicator 10, the expulsion member 16 is pushed into the barrel 14 to expel the tampon 12 from the barrel 14, and into the vagina. The applicator 10 is then withdrawn from the vagina and may be discarded.

While the detailed description above relates to a preferred embodiment of insertion devices, i.e., a tampon applicator, one of ordinary skill in the art will readily recognize that the same device can be used for the vaginal or rectal delivery of prophylactic compositions, such as spermicides, and/or medicaments, such as fungicides. These compositions and/or medicaments may be in the form of solids, creams, foams, gels, and the like.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. A method of forming a flexible applicator useful for inserting an article into a mammalian body cavity comprising the steps of:
   a) forming flex-enhancing elements in a structural member, the structural member having an outer surface, an insertion end, and an opposed gripper end comprising at least one grip-enhancing feature, wherein the flex-enhancing elements are arranged and configured intermediate the insertion and gripper ends;
   b) superposing a layer of a flexible material on the outer surface of the structural member; and
   c) forming the structural member into an elongate, hollow member suitable for containing the insertable article.

2. The method of claim 1 wherein the step of superposing the layer of flexible material comprises (i) applying a laminating material to the outer surface of the structural member and (ii) applying the layer of flexible material to the laminating material.

3. The method of claim 1 wherein the step of forming the flex-enhancing elements comprises perforating the structural member.

4. The method of claim 3 wherein the step of perforating the structural member comprises slitting the structural member.

5. The method of claim 1 wherein the step of forming an elongate, hollow member comprises forming a cylindrical tube.

6. The method of claim 5 wherein the tube is a convolutely wound tube.

7. The method of claim 5 wherein the tube is a spirally wound tube.

8. The method of claim 5 wherein the tube is a longitudinally seamed tube.

9. The method of claim 1 which further comprises the step of substantially closing the insertion end of the hollow member.

10. The method of claim 1 wherein the step of superposing the layer of the flexible material comprises spanning the flex-enhancing elements with the layer of flexible material.

11. A method of forming a flexible applicator useful for inserting an article into a mammalian body cavity comprising the steps of:
    a) forming flex-enhancing elements in a structural member, the structural member having an outer surface, an insertion end, and an opposed gripper end having an opening therein and comprising at least one grip-enhancing feature, wherein the flex-enhancing elements are arranged and configured intermediate the insertion and gripper ends; and
    b) forming the structural member into an elongate hollow member suitable for containing the insertable article.

* * * * *